United States Patent
Tani et al.

(10) Patent No.: US 12,408,828 B2
(45) Date of Patent: Sep. 9, 2025

(54) IMAGING DEVICE AND ENDOSCOPE SYSTEM

(71) Applicant: OLYMPUS MEDICAL SYSTEMS CORP., Hachioji (JP)

(72) Inventors: Takaharu Tani, Hachioji (JP); Keisuke Ogawa, Hachioji (JP); Yasunari Harada, Hachioji (JP)

(73) Assignee: OLYMPUS MEDICAL SYSTEMS CORP., Tokyo (JP)

(*) Notice: Subject to any disclaimer, the term of this patent is extended or adjusted under 35 U.S.C. 154(b) by 369 days.

(21) Appl. No.: 18/189,627

(22) Filed: Mar. 24, 2023

(65) Prior Publication Data
US 2023/0225600 A1 Jul. 20, 2023

Related U.S. Application Data

(63) Continuation of application No. PCT/JP2020/036527, filed on Sep. 28, 2020.

(51) Int. Cl.
A61B 1/00 (2006.01)
A61B 1/045 (2006.01)
A61B 1/05 (2006.01)

(52) U.S. Cl.
CPC .......... *A61B 1/05* (2013.01); *A61B 1/045* (2013.01); *A61B 1/00009* (2013.01)

(58) Field of Classification Search
CPC ....... A61B 1/05; A61B 1/045; A61B 1/00009; A61B 1/00004; A61B 1/00025; A61B 1/00027; H04N 5/63; G02B 23/2492
See application file for complete search history.

(56) References Cited

U.S. PATENT DOCUMENTS 10,778,933 B2 * 9/2020 Shigehisa .......... G02B 23/2492

FOREIGN PATENT DOCUMENTS

| JP | 2008-161427 A | 7/2008 |
| JP | 2011-206333 A | 10/2011 |
| JP | 2016-214381 A | 12/2016 |
| JP | 2016-214571 A | 12/2016 |

OTHER PUBLICATIONS

International Search Report dated Nov. 2, 2020, issued in counterpart Application No. PCT/JP2020/036527 with English translation. (4 pages).

* cited by examiner

Primary Examiner — Timothy J Neal
(74) Attorney, Agent, or Firm — WHDA, LLP

(57) ABSTRACT

An imaging device includes a camera unit and a control unit. The camera unit includes an image sensor. The control unit includes a voltage measurement circuit and a voltage adjustment circuit. A first power source voltage is transferred from the control unit to the camera unit by a power source line and is input to the camera unit as a second power source voltage. A video signal or the second power source voltage is output to a video signal line. The voltage measurement circuit is configured to measure a voltage value of the second power source voltage. The voltage adjustment circuit is configured to adjust a value of the first power source voltage based on the value of the second power source voltage.

8 Claims, 9 Drawing Sheets

ND ENDOSCOPE
IMAGING DEVICE AND ENDOSCOPE SYSTEM

The present application is a continuation application based on International Patent Application No. PCT/JP2020/036527 filed on Sep. 28, 2020, the content of which is incorporated herein by reference.

BACKGROUND OF THE INVENTION

Field of the Invention

The present invention relates to an imaging device and an endoscope system.

Description of Related Art

An endoscope system includes an endoscope (camera unit) and a main body, and the endoscope and the main body are connected to each other by a cable. An imager is mounted in the distal end of the endoscope. A power source voltage used for driving the imager is transferred from the main body to the distal end of the endoscope via the cable. Hereinafter, the power source voltage that has reached the distal end of the endoscope will be called a distal end voltage.

The power source voltage needs to be adjusted such that the distal end voltage has an appropriate value in order to drive the imager stably. However, the value of the distal end voltage may deviate from a voltage range recommended for an operation of the imager due to factors such as the length of the cable, deviations and fluctuations of the characteristics of the cable, and fluctuations of a current used for driving the imager. Hereinafter, the voltage range recommended for the operation of the imager will be called a recommended voltage range. As a result, problems may occur in driving the imager stably. Particularly, when the cable is long or thin, the influence thereof becomes noticeable and it is highly probable that the value of the distal end voltage deviates from the recommended voltage range.

In the prior art, a high-power source voltage is output to the cable in order for the value of the distal end voltage to fall in the recommended voltage range. However, since the accuracy and the follow-up performance are low, a problem occurs in that the image quality deteriorates and heat is generated. In addition, a problem also occurs in that the thickness of the cable increases in order to reduce the difference between the voltage of the main body and the voltage of the distal end of the endoscope. Accordingly, there is a demand for providing the endoscope with a power source voltage in the narrowest possible range.

A technique disclosed in Japanese Unexamined Patent Application, First Publication No. 2011-206333 provides a function of adjusting a power source voltage based on the distal end voltage. According to the technique, the distal end voltage is monitored at all times by using a dedicated cable for determining the distal end voltage, and the power source voltage is adjusted such that the distal end voltage has an appropriate value.

SUMMARY OF THE INVENTION

According to a first aspect of the present invention, an imaging device includes a camera unit and a control unit connected to each other by a power source line that transfers a first power source voltage and a video signal line that transfers a video signal. The first power source voltage transferred by the power source line is input to the camera unit as a second power source voltage. The camera unit includes an image sensor and a load circuit. The image sensor is configured to generate the video signal. The control unit includes a signal reception circuit, a voltage generation circuit, a voltage measurement circuit, and a voltage adjustment circuit. The signal reception circuit is configured to receive the video signal. The voltage generation circuit is configured to output the first power source voltage to the power source line. The voltage measurement circuit is configured to measure a value of the second power source voltage. The voltage adjustment circuit is configured to adjust a value of the first power source voltage by controlling the power source voltage generation circuit based on the value of the second power source voltage. The imaging device further includes a setting circuit configured to set the camera unit to be in a first state in a first period and set the camera unit to be in a second state in a second period different from the first period. The video signal generated by the image sensor is output to the video signal line in the first state. Output of the video signal from the image sensor to the video signal line is stopped in the second state. The load circuit is configured to consume the second power source voltage as a current in the second state. The second power source voltage is output to the video signal line in the second state. Output of the second power source voltage to the video signal line is stopped in the first state. The voltage measurement circuit is configured to measure the value of the second power source voltage transferred by the video signal line.

According to a second aspect of the present invention, in the first aspect, the setting circuit may include a first switching circuit and a second switching circuit. The first switching circuit is disposed in the camera unit and is configured to connect the power source line and the video signal line to each other in the second period and disconnect the power source line and the video signal line from each other in the first period. The second switching circuit is disposed in the control unit and is configured to connect the video signal line and the signal reception circuit to each other in the first period, disconnect the video signal line and the signal reception circuit from each other in the second period, connect the video signal line and the voltage measurement circuit to each other in the second period, and disconnect the video signal line and the voltage measurement circuit from each other in the first period.

According to a third aspect of the present invention, in the second aspect, the imaging device may further include a resistance circuit including the voltage measurement circuit. The resistance circuit may have a greater resistance value than a resistance value of the video signal line. The second switching circuit may be configured to connect the video signal line and the resistance circuit to each other in the second period and disconnect the video signal line and the resistance circuit from each other in the first period.

According to a fourth aspect of the present invention, in the first aspect, the camera unit may further include a transmission buffer configured to enter any one of a third state and a fourth state. When a state of the transmission buffer is the third state, the transmission buffer may be configured to output the video signal generated by the image sensor to the video signal line. When the state of the transmission buffer is the fourth state, the transmission buffer may be configured to stop output of the video signal to the video signal line. The setting circuit may be configured to set the state of the transmission buffer to the third state in the first period and set the state of the transmission buffer to the fourth state in the second period.

According to a fifth aspect of the present invention, in the first aspect, the voltage adjustment circuit may be configured to calculate a resistance value of the power source line based on the value of the first power source voltage, the value of the second power source voltage, and a value of a current that flows through the power source line and adjust the value of the first power source voltage based on the resistance value.

According to a sixth aspect of the present invention, an endoscope system includes both a scope that has a distal end and is to be inserted into a living body and the imaging device. The camera unit is disposed in the distal end.

According to a seventh aspect of the present invention, an imaging device includes a camera unit and a control unit connected to each other by a power source line that transfers a first power source voltage, a video signal line that transfers a video signal, and a control line that transfers a control signal. The first power source voltage transferred by the power source line is input to the camera unit as a second power source voltage. The camera unit includes an image sensor and a load circuit. The image sensor is configured to generate the video signal in accordance with the control signal. The control unit includes a signal reception circuit, a control signal generation circuit, a voltage generation circuit, a voltage measurement circuit, and a voltage adjustment circuit. The signal reception circuit is configured to receive the video signal. The control signal generation circuit is configured to generate the control signal and output the generated control signal to the control signal line. The voltage generation circuit is configured to output the first power source voltage to the power source line. The voltage measurement circuit is configured to measure a value of the second power source voltage. The voltage adjustment circuit is configured to adjust a value of the first power source voltage by controlling the power source voltage generation circuit based on the value of the second power source voltage. The imaging device further includes a setting circuit configured to set the camera unit to be in a first state in a first period and set the camera unit to be in a second state in a second period different from the first period. The control signal is output to the control signal line in the first state. Output of the control signal to the control signal line is stopped in the second state. The load circuit is configured to consume the second power source voltage as a current in the second state. The second power source voltage is output to the control signal line in the second state. Output of the second power source voltage to the control signal line is stopped in the first state. The voltage measurement circuit is configured to measure the value of the second power source voltage transferred by the control signal line.

According to an eighth aspect of the present invention, an imaging device includes a camera unit and a control unit connected to each other by a power source line that transfers a first power source voltage, a video signal line that transfers a video signal, and a control line that transfers a control signal. The first power source voltage transferred by the power source line is input to the camera unit as a second power source voltage. The camera unit includes an image sensor and a load circuit. The image sensor is configured to generate the video signal in accordance with the control signal. The control unit includes a signal reception circuit, a control signal generation circuit, a voltage generation circuit, a voltage measurement circuit, and a voltage adjustment circuit. The signal reception circuit is configured to receive the video signal. The control signal generation circuit is configured to generate the control signal and output the generated control signal to the control signal line. The voltage generation circuit is configured to output the first power source voltage to the power source line. The voltage measurement circuit is configured to measure a value of the second power source voltage. The voltage adjustment circuit is configured to adjust a value of the first power source voltage by controlling the power source voltage generation circuit based on the value of the second power source voltage. Any one of the power source line, the video signal line, and the control signal line includes a first signal line and a second signal line connected in parallel to the camera unit and the control unit. The imaging device further includes a setting circuit configured to set the camera unit to be in a first state in a first period and set the camera unit to be in a second state in a second period different from the first period. Any one of the first power source voltage, the video signal, and the control signal is transferred by the first signal line and the second signal line in the first state. The load circuit is configured to consume the second power source voltage as a current in the second state. The second power source voltage is output to any one of the first signal line and the second signal line in the second state. The voltage measurement circuit is configured to measure the value of the second power source voltage transferred by any one of the first signal line and the second signal line.

DETAILED DESCRIPTION OF THE INVENTION

Hereinafter, embodiments of the present invention will be described with reference to the drawings. Each of the embodiments will be described in detail by using an endoscope system as an example of an imaging device.

First Embodiment

Figure 1:
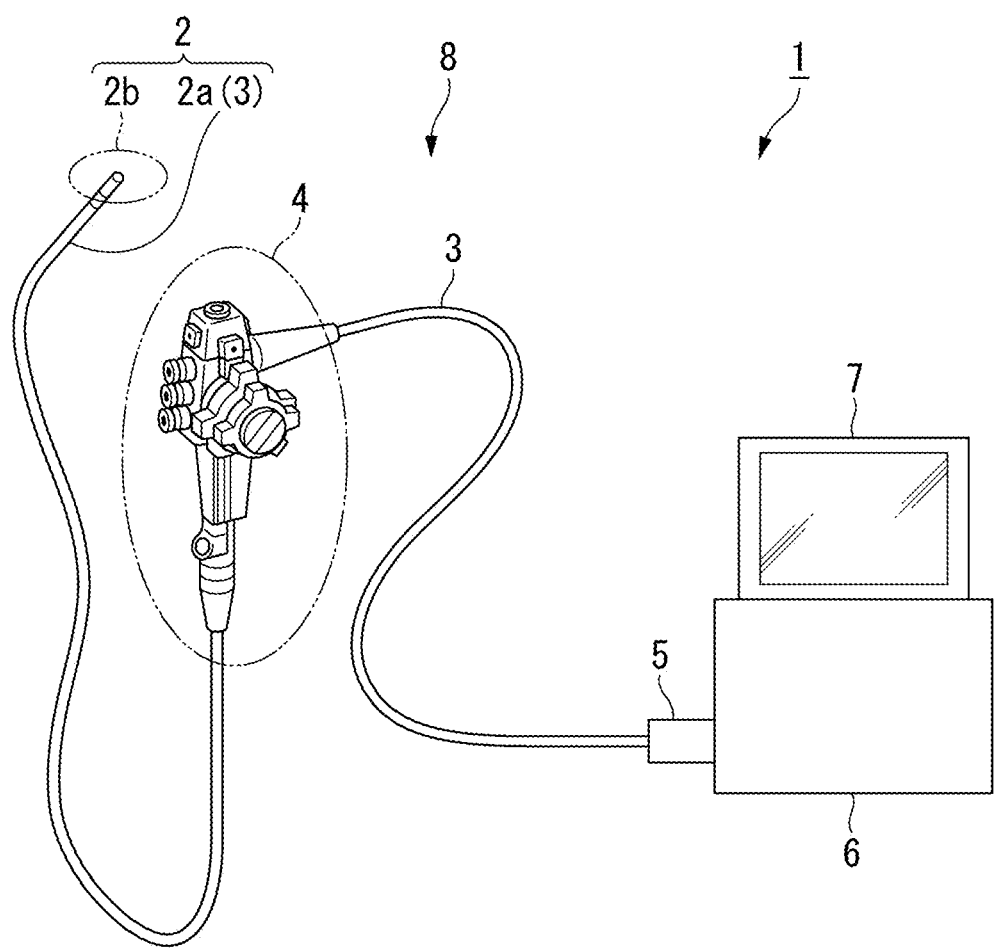
FIG. 1 is a schematic diagram showing a configuration of an endoscope system according to a first embodiment of the present invention.

FIG. 1 shows a configuration of an endoscope system 1 according to a first embodiment of the present invention.

The endoscope system 1 shown in FIG. 1 includes an endoscope insertion unit 2, a transmission cable 3, an operation unit 4, a connector unit 5, a processor 6, and a display device 7. The endoscope insertion unit 2, the transmission cable 3, the operation unit 4, and the connector unit 5 constitute a scope.

Figure 2:
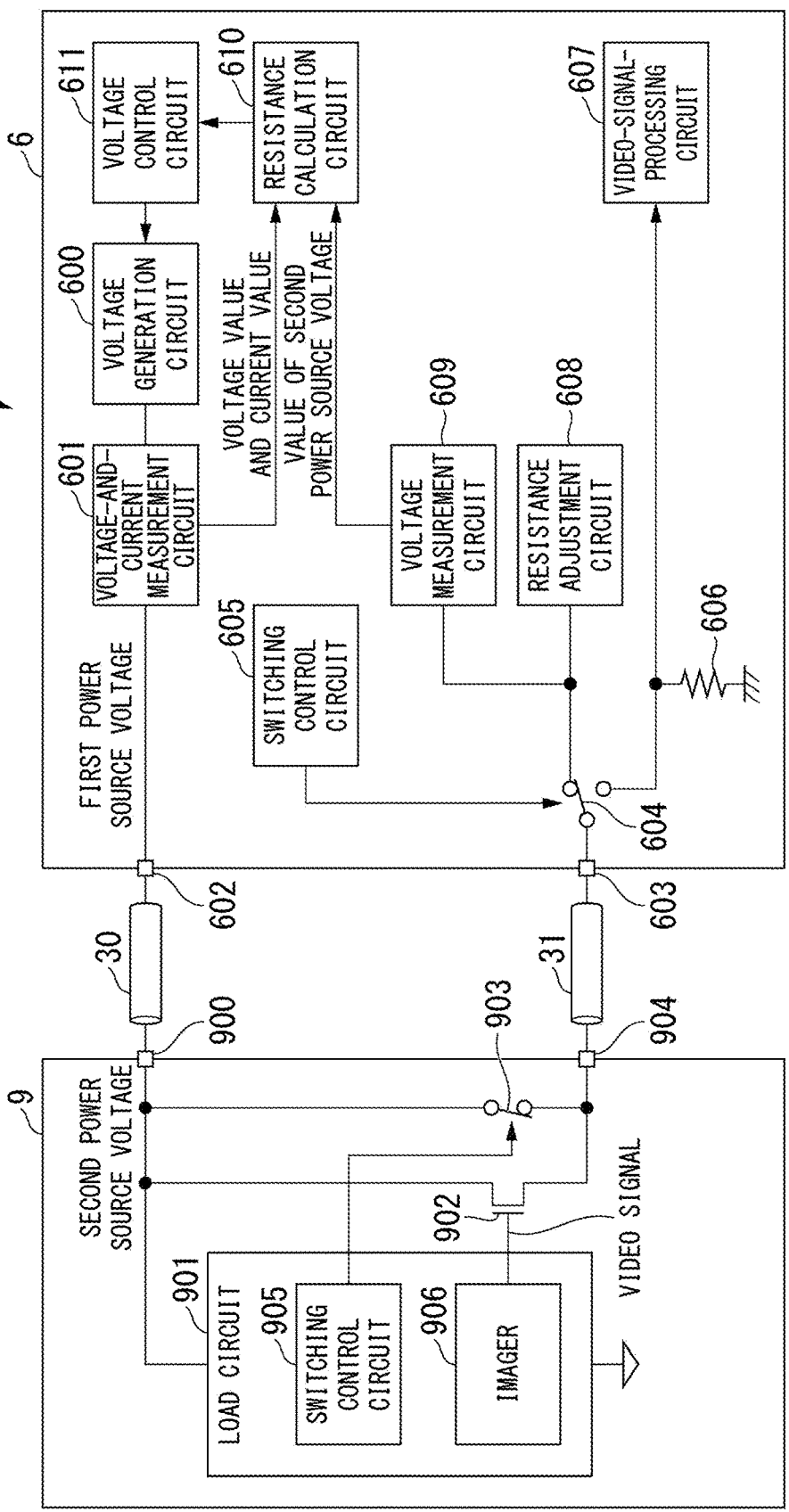
FIG. 2 is a block diagram showing a configuration of the endoscope system according to the first embodiment of the present invention.

The endoscope insertion unit 2 includes an insertion unit 2a. The insertion unit 2a is part of the transmission cable 3. The insertion unit 2a is to be inserted inside a living body, which is a subject. The endoscope insertion unit 2 generates a video signal by imaging the inside of the subject. The endoscope insertion unit 2 outputs the generated video signal to the processor 6. A camera unit 9 shown in FIG. 2 is disposed in a distal end 2b of the insertion unit 2a. In the insertion unit 2a, the operation unit 4 is connected to the end part opposite the distal end 2b. The operation unit 4 receives various operations for the endoscope insertion unit 2 from a user.

The transmission cable 3 connects the camera unit 9 and the connector unit 5. The video signal generated by the camera unit 9 is output to the connector unit 5 via the transmission cable 3.

The connector unit 5 is connected to the endoscope insertion unit 2 and the processor 6. The connector unit 5 performs predetermined processing on the video signal output from the endoscope insertion unit 2. The connector unit 5 outputs the video signal to the processor 6.

The processor 6 performs image processing on the video signal output from the connector unit 5. Furthermore, the processor 6 centrally controls the entire endoscope system 1.

The display device 7 displays a video based on the video signal processed by the processor 6. In addition, the display device 7 displays various kinds of information related to the endoscope system 1.

The endoscope system 1 includes a light source device that generates illumination light emitted to the subject. The light source device is not shown in FIG. 1.

FIG. 2 shows an internal configuration of the endoscope system 1. The endoscope system 1 shown in FIG. 2 includes the camera unit 9 and the processor 6. The camera unit 9 is disposed in the distal end 2b of the scope. The operation unit 4, the connector unit 5, and the display device 7 are not shown in FIG. 2. The transmission cable 3 shown in FIG. 1 includes a power source line 30 and a video signal line 31 shown in FIG. 2.

The camera unit 9 includes a power source terminal 900, a load circuit 901, a transmission buffer 902, a switch 903, and a video terminal 904. The load circuit 901 includes a switching control circuit 905 and an imager 906. At least one of the transmission buffer 902, the switch 903, and the switching control circuit 905 may be disposed in the imager 906.

The processor 6 includes a voltage generation circuit 600, a voltage-and-current measurement circuit 601, a power source terminal 602, a video terminal 603, a switch 604, a switching control circuit 605, a resistor 606, a video-signal-processing circuit 607, a resistance adjustment circuit 608, a voltage measurement circuit 609, a resistance calculation circuit 610, and a voltage control circuit 611. The processor 6 is a control unit. All or part of the configuration of the processor 6 shown in FIG. 2 may be disposed in the operation unit 4 or the connector unit 5 shown in FIG. 1.

A schematic configuration of the endoscope system 1 will be described. The camera unit 9 and the processor 6 are connected to each other by both the power source line 30 that transfers a first power source voltage and the video signal line 31 that transfers a video signal. The first power source voltage transferred by the power source line 30 is input to the camera unit 9 as a second power source voltage. The imager 906 generates a video signal by using the second power source voltage. The video-signal-processing circuit 607 (signal reception circuit) receives the video signal transferred by the video signal line 31. The voltage generation circuit 600 generates a first power source voltage and outputs the generated first power source voltage to the power source line 30. The voltage measurement circuit 609 measures a value of the second power source voltage. The voltage control circuit 611 and the resistance calculation circuit 610 (voltage adjustment circuit) adjusts a value of the first power source voltage based on the value of the second power source voltage.

The switch 903 and the switch 604 (setting circuit) set the camera unit 9 and the processor 6 to be in a first state in a first period and set the camera unit 9 and the processor 6 to be in a second state in a second period different from the first period. The video signal generated by the imager 906 is output to the video signal line 31 in the first state. The output of the video signal from the imager 906 to the video signal line 31 is stopped in the second state. The load circuit 901 consumes the second power source voltage as a current in the second state. The second power source voltage is output to the video signal line 31 in the second state. The output of the second power source voltage to the video signal line 31 is stopped in the first state. The voltage measurement circuit 609 measures a value of the second power source voltage transferred by the video signal line 31.

A detailed configuration of the endoscope system 1 will be described. For example, the voltage generation circuit 600 is a voltage regulator. The voltage generation circuit 600 generates the first power source voltage, which is a direct-current (DC) voltage. The voltage-and-current measurement circuit 601 measures both a value (voltage value) of the first power source voltage generated by the voltage generation circuit 600 and a value (current value) of a current (DC current) that flows through the power source line 30. The voltage-and-current measurement circuit 601 outputs the measured voltage value and current value to the resistance calculation circuit 610.

The first power source voltage generated by the voltage generation circuit 600 is input to the power source terminal 602 via the voltage-and-current measurement circuit 601. The power source terminal 602 is connected to the power source line 30. The power source terminal 602 outputs the first power source voltage to the power source line 30. The power source line 30 is a signal line disposed in the transmission cable 3. The power source line 30 transfers the first power source voltage output from the power source terminal 602 to the camera unit 9.

The power source terminal 900 is connected to the power source line 30. The first power source voltage transferred by the power source line 30 is input to the power source terminal 900. The power source terminal 900 outputs the first power source voltage to each circuit in the camera unit 9 as the second power source voltage. The second power source voltage is a power source voltage transferred by the power source line 30 to the camera unit 9 and is a voltage on a path including a path from the power source terminal 900 to the imager 906. A voltage drop is generated due to the DC resistance of the power source line 30, and the second power source voltage is attenuated. Therefore, the value of the second power source voltage is less than that of the first power source voltage in the processor 6.

The load circuit 901 is connected to the power source terminal 900. The load circuit 901 has a DC resistance value and consumes the second power source voltage as a current. The imager 906 is an image sensor such as a complementary metal-oxide semiconductor (CMOS) sensor. The imager 906 includes a plurality of pixels and generates a video signal having a voltage generated based on the second power source voltage.

In the example shown in FIG. 2, the load circuit 901 includes the imager 906. The load circuit 901 does not need to include the imager 906. The load circuit 901 may include only the imager 906.

For example, the transmission buffer 902 is a transistor including a gate terminal, a source terminal, and a drain terminal and constitutes a source follower. The gate terminal of the transmission buffer 902 is connected to the imager 906. One of the source terminal and the drain terminal of the transmission buffer 902 is connected to the power source terminal 900, and the other of the source terminal and the drain terminal of the transmission buffer 902 is connected to the video terminal 904.

The switch 903 (first switching circuit) constitutes a setting circuit. The switch 903 is connected to the power source terminal 900 and the video terminal 904. The switch 903 connects the power source line 30 and the video signal line 31 to each other in the second period and disconnects the power source line 30 and the video signal line 31 from each other in the first period. For example, the first period is a period during which the imager 906 outputs the video signal. The second period is all or part of a period excluding the first period. For example, the second period is a blanking period. The blanking period is at least one of a horizontal blanking period and a vertical blanking period.

The switch 903 enters any one of an ON state and an OFF state. The switch 903 can switch between the ON state and the OFF state. When the state of the switch 903 is the ON state, the switch 903 connects the power source line 30 and the video signal line 31 to each other. When the state of the switch 903 is the OFF state, the switch 903 disconnects the power source line 30 and the video signal line 31 from each other.

The switching control circuit 905 outputs a switching control signal to the switch 903, thus controlling the state of the switch 903. The switching control circuit 905 sets the state of the switch 903 to the OFF state in the first period. At this time, the transmission buffer 902 outputs the video signal to the video terminal 904. The switching control circuit 905 sets the state of the switch 903 to the ON state in the second period. At this time, the power source line 30 and the video signal line 31 are short-circuited, and the second power source voltage is output to the video terminal 904. The voltages of the source terminal and the drain terminal of the transmission buffer 902 become almost the same, and the transmission buffer 902 stops the output of the video signal.

The video terminal 904 is connected to the video signal line 31. The video terminal 904 outputs the video signal or the second power source voltage to the video signal line 31. The video signal line 31 is a signal line disposed in the transmission cable 3. The video signal line 31 transfers the video signal output from the transmission buffer 902 to the processor 6 in the first period. The video signal line 31 transfers the second power source voltage output from the power source terminal 900 to the processor 6 in the second period.

The video terminal 603 is connected to the video signal line 31. The video signal or the second power source voltage transferred by the video signal line 31 is input to the video terminal 603.

The switch 604 (second switching circuit) constitutes a setting circuit. The switch 604 is connected to the video terminal 603, the voltage measurement circuit 609, and the video-signal-processing circuit 607. The switch 604 connects the video signal line 31 and the video-signal-processing circuit 607 to each other in the first period and disconnects the video signal line 31 and the video-signal-processing circuit 607 from each other in the second period. The switch 604 connects the video signal line 31 and the voltage measurement circuit 609 to each other in the second period and disconnects the video signal line 31 and the voltage measurement circuit 609 from each other in the first period.

The switch 604 enters any one of a video output state and a power source output state. The switch 604 can switch between the video output state and the power source output state. When the state of the switch 604 is the video output state, the switch 604 connects the video signal line 31 and the video-signal-processing circuit 607 to each other and disconnects the video signal line 31 and the voltage measurement circuit 609 from each other. When the state of the switch 604 is the power source output state, the switch 604 disconnects the video signal line 31 and the video-signal-processing circuit 607 from each other and connects the video signal line 31 and the voltage measurement circuit 609 to each other.

The switching control circuit 605 outputs a switching control signal to the switch 604, thus controlling the state of the switch 604. The switching control circuit 605 sets the state of the switch 604 to the video output state in the first period. At this time, the video signal transferred by the video signal line 31 and input to the video terminal 603 is output to the video-signal-processing circuit 607 via the switch 604. The switching control circuit 605 sets the state of the switch 604 to the power source output state in the second period. At this time, the second power source voltage transferred by the video signal line 31 and input to the video terminal 603 is output to the voltage measurement circuit 609 via the switch 604.

The resistor 606 is connected to the switch 604 and the video-signal-processing circuit 607. The resistor 606 is a terminal resistor. The video signal is input to the video-signal-processing circuit 607 in the first period. For example, the video-signal-processing circuit 607 is an analog front end (AFE). The video-signal-processing circuit 607 receives the video signal and performs predetermined signal processing on the video signal. In a case in which the resistor 606 is unnecessary or has a high resistance value, the switch 604 and the switching control circuit 605 are not necessarily disposed.

The resistance adjustment circuit 608 and the voltage measurement circuit 609 are connected to the switch 604. The resistance adjustment circuit 608 and the voltage measurement circuit 609 constitute a resistance circuit having a DC resistance value. The resistance value of the input terminal (the input terminal of the voltage measurement circuit 609) of the resistance circuit is extremely high, and the resistance circuit is in a high-impedance state (Hi-Z). The second power source voltage is input to the input terminal of the resistance circuit in the second period.

Since the resistance circuit is in the high-impedance state, a current hardly flows through the video signal line 31 in the second period and the value of the second power source voltage input to the resistance circuit is almost the same as that of the second power source voltage input to the power source terminal 900 in the camera unit 9.

The resistance circuit needs to have at least a greater resistance value than that of the video signal line 31. The resistance value of the video signal line 31 and an approximate resistance value of the load circuit 901 are known. The switch 604 connects the video signal line 31 and the resistance circuit to each other in the second period and disconnects the video signal line 31 and the resistance circuit from each other in the first period.

For example, the resistance adjustment circuit 608 is an input impedance of the voltage measurement circuit 609 or a capacitance element through which a DC current does not flow.

The voltage measurement circuit 609 measures a value of the second power source voltage in the second period. The voltage measurement circuit 609 outputs the measured value of the second power source voltage to the resistance calculation circuit 610. The video-signal-processing circuit 607 may also have the function of the voltage measurement circuit 609.

The resistance calculation circuit 610 and the voltage control circuit 611 constitute a voltage adjustment circuit. The resistance calculation circuit 610 calculates a resistance value (DC resistance value) of the power source line 30 based on the value of the first power source voltage, the value of the second power source voltage, and the value of the current that flows through the power source line 30. These values meet a condition shown in the following Expression (1).

$$VDD - Vcis = Rcable * Ivdd \quad (1)$$

In Expression (1), a value VDD indicates the value of the first power source voltage, a value Vcis indicates the value of the second power source voltage, a resistance value Rcable indicates the resistance value of the power source line 30, and a current value Ivdd indicates the value of the current that flows through the power source line 30. Accordingly, the resistance calculation circuit 610 can calculate the resistance value Rcable in accordance with the following Expression (2).

$$Rcable = (VDD - Vcis)/Ivdd \quad (2)$$

The resistance calculation circuit 610 calculates a control value of the first power source voltage by using the calculated resistance value. The resistance calculation circuit 610 outputs the calculated control value to the voltage control circuit 611. The voltage control circuit 611 controls the voltage generation circuit 600 based on the control value, thus adjusting a value of the first power source voltage to be generated by the voltage generation circuit 600. For example, when the resistance value Rcable decreases, the amount of the voltage drop in the power source line 30 decreases and the value of the second power source voltage increases. Therefore, the voltage control circuit 611 reduces the value of the first power source voltage. When the resistance value Rcable increases, the amount of the voltage drop in the power source line 30 increases and the value of the second power source voltage decreases. Therefore, the voltage control circuit 611 increases the value of the first power source voltage. In addition, when the current value measured by the voltage-and-current measurement circuit 601 increases, the amount of the voltage drop in the power source line 30 increases and the value of the second power source voltage decreases. Therefore, the voltage control circuit 611 increases the value of the first power source voltage. When the current value measured by the voltage-and-current measurement circuit 601 decreases, the amount of the voltage drop in the power source line 30 decreases and the value of the second power source voltage increases. Therefore, the voltage control circuit 611 reduces the value of the first power source voltage.

The voltage control circuit 611 adjusts the value of the first power source voltage such that the value of the second power source voltage input to the power source terminal 900 matches a recommended voltage value for the operation of the imager 906. For example, the recommended voltage value is 3.3 V. The value VDD of the first power source voltage, the value Vcis of the second power source voltage, the current value Ivdd, and the resistance value Rcable meet the condition shown in Expression (1) described above. In order for the value Vcis of the second power source voltage to be 3.3 V, a condition shown in the following Expression (3) needs to be met. The voltage control circuit 611 controls the voltage generation circuit 600 such that the value of the first power source voltage to be generated by the voltage generation circuit 600 matches a value VDD' shown in Expression (3).

$$VDD' = 3.3 + Rcable * Ivdd \quad (3)$$

In addition, by considering Expression (1) and Expression (3), the value VDD' is also expressed by Expression (4). The resistance calculation circuit 610 and the voltage control circuit 611 may control the voltage generation circuit 600 in accordance with Expression (4).

$$VDD' = 3.3 + VDD - Vcis \quad (4)$$

Figure 3:
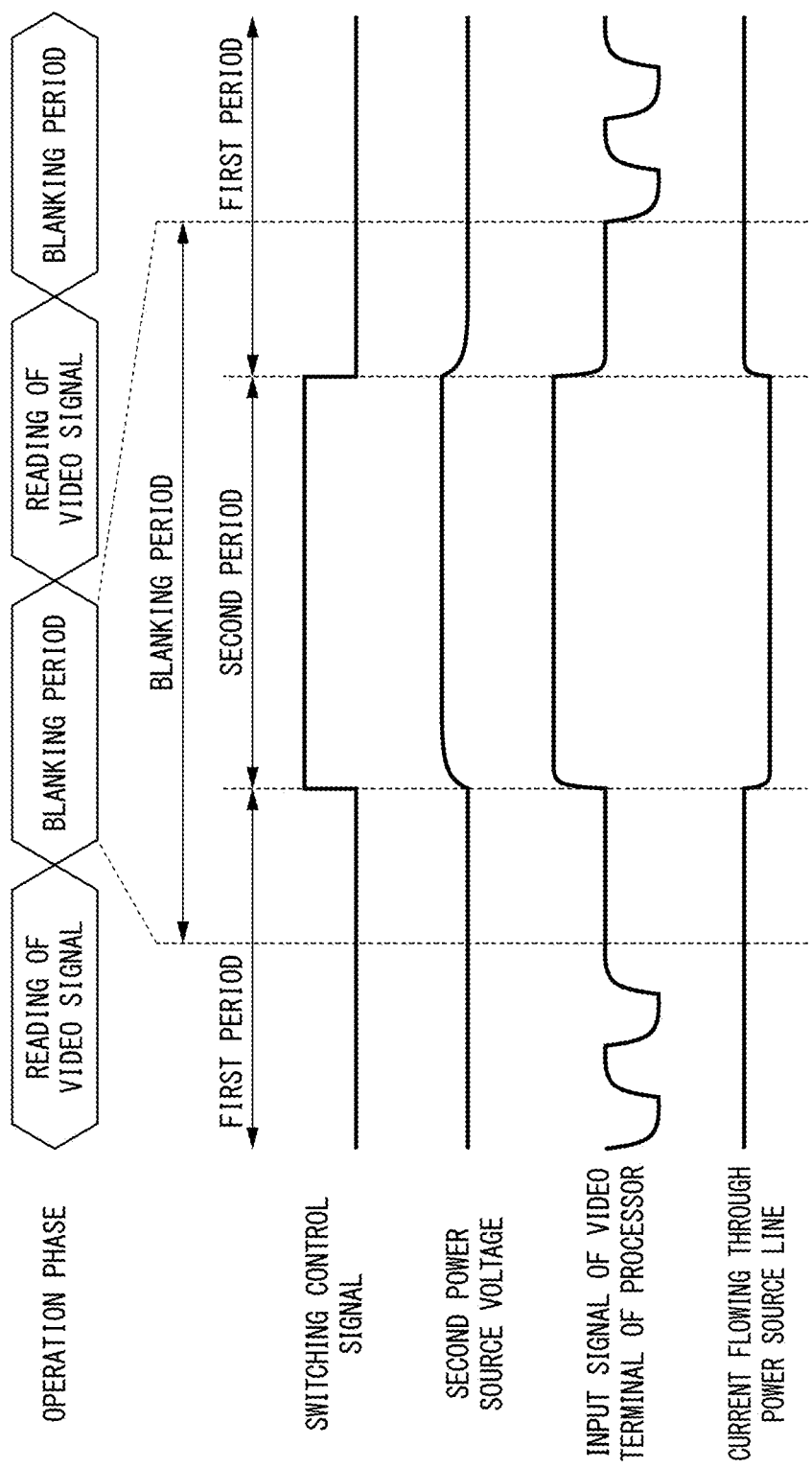
FIG. 3 is a timing chart showing an operation of the endoscope system according to the first embodiment of the present invention.

FIG. 3 shows an operation of the endoscope system 1. In FIG. 3, an operation phase of the imager 906 is shown. In addition, waveforms of the switching control signal input to the switch 903 or the switch 604, the second power source voltage output from the power source terminal 900, the signal input to the video terminal 603, and the current that flows through the power source line 30 are shown in FIG. 3. The horizontal direction in FIG. 3 indicates time, and the vertical direction in FIG. 3 indicates a voltage value or a current value.

The operation phase of the imager 906 repeats reading of the video signal and a blanking period. The blanking period periodically occurs. While the imager 906 outputs the video signal in the first period, the voltage of the switching control signal is a low level. At this time, the state of the switch 903 is the OFF state, and the state of the switch 604 is the video output state. Therefore, the video signal line 31 transfers the video signal, and the video-signal-processing circuit 607 receives the video signal.

When the blanking period is started, the imager 906 stops the output of the video signal. The voltage of the switching control signal changes to a high level in the blanking period. At this time, the first period is completed, and the second period is started. The state of the switch 903 changes to the ON state, and the state of the switch 604 changes to the power source output state. Therefore, the video signal line 31 transfers the second power source voltage, and the second power source voltage is input to the voltage measurement circuit 609. The voltage measurement circuit 609 measures a value of the second power source voltage.

The video signal passes through the video signal line 31 in the first period, and a current flows through the video signal line 31. On the other hand, the current hardly flows through the video signal line 31 in the second period. The value of the current that flows through the video signal line 31 in the second period is less than that in the first period. Therefore, the value of the current that flows through the power source line 30 in the second period is less than that in the first period. If the current that flows through the power source line 30 is reduced, the amount of the voltage drop in the power source line 30 is reduced. Therefore, the value of the second power source voltage in the second period is greater than that in the first period.

The voltage of the switching control signal changes to the low level before the blanking period is completed. At this time, the second period is completed, and the first period is started. The state of the switch 903 changes to the OFF state, and the state of the switch 604 changes to the video output state. Therefore, the output of the second power source voltage to the video signal line 31 is stopped.

When the blanking period is completed, the imager 906 starts the output of the video signal. The video signal line 31 transfers the video signal, and the video-signal-processing circuit 607 receives the video signal.

In one or more of two or more blanking periods that periodically occur, the voltage measurement circuit 609 calculates a value of the second power source voltage and the resistance calculation circuit 610 calculates a resistance value of the power source line 30. Each time a blanking period occurs, the voltage measurement circuit 609 does not need to calculate a value of the second power source voltage and the resistance calculation circuit 610 does not need to calculate a resistance value of the power source line 30.

In the first embodiment, the endoscope system 1 can monitor a power source voltage (second power source voltage) provided to the imager 906. The video signal line 31 is used for transferring the video signal and the second power source voltage, and the endoscope system 1 does not need to monitor the second power source voltage at all times. Therefore, a dedicated cable for transferring the second power source voltage is unnecessary, and the miniaturization of the camera unit 9 is not prevented.

The endoscope system 1 can calculate the amount of a voltage drop in the power source line 30 by calculating the resistance value of the power source line 30. The endoscope system 1 can directly adjust the value of the first power source voltage to be generated by the voltage generation circuit 600 by controlling the voltage generation circuit 600 based on the amount.

A switch through which a large current flows has a large area. Since a current hardly flows through the switch 903 in the second period, the switch 903 does not need to have a large area. In addition, since a switch capable of switching between the ON state and the OFF state is used as the switch 903, the switch 903 can be miniaturized.

Second Embodiment

Figure 4:
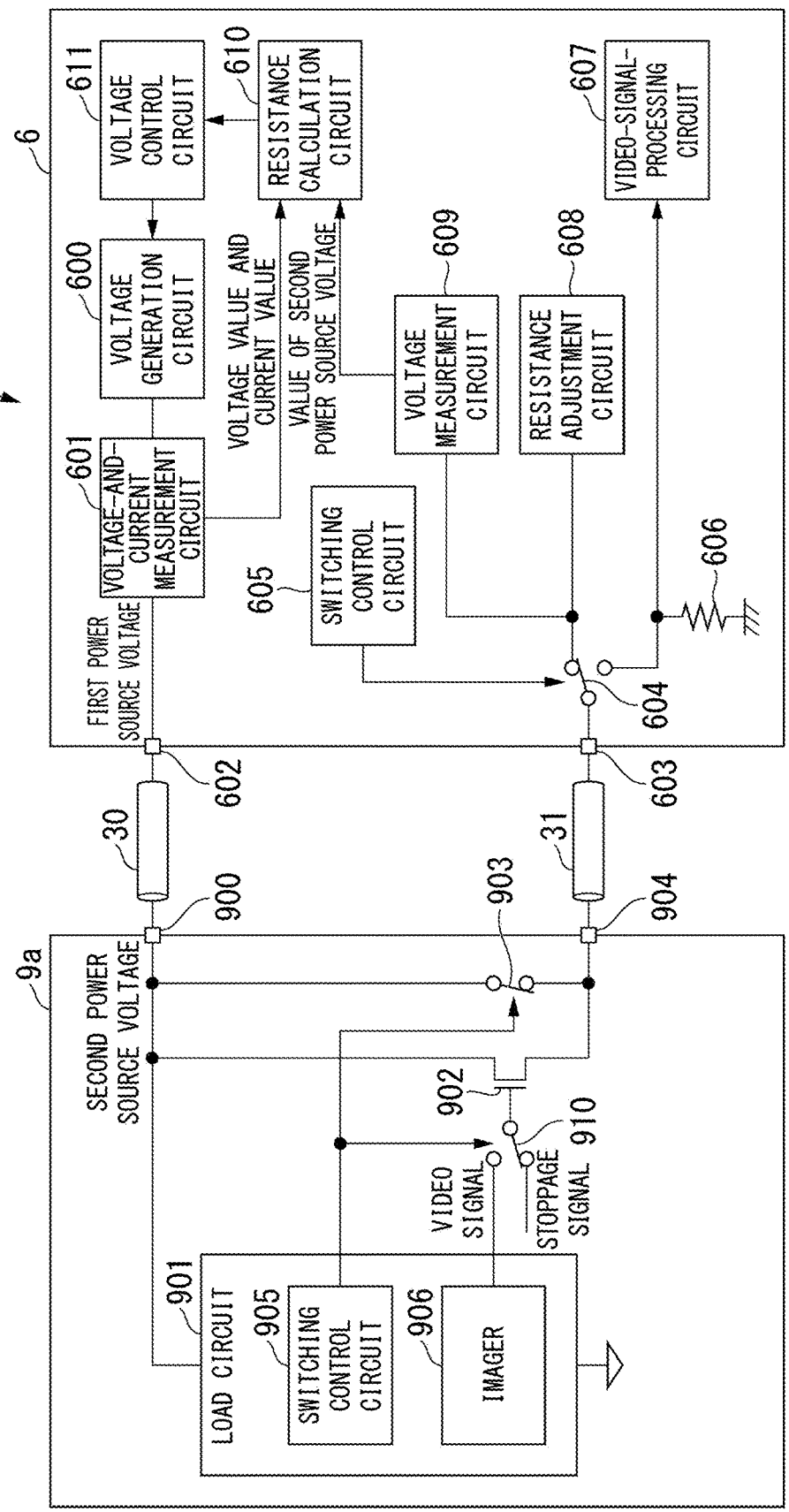
FIG. 4 is a block diagram showing a configuration of an endoscope system according to a second embodiment of the present invention.

FIG. 4 shows an internal configuration of an endoscope system 1a according to a second embodiment of the present invention. The same configuration as that shown in FIG. 2 will not be described. The endoscope system 1a shown in FIG. 4 includes a camera unit 9a and a processor 6.

The camera unit 9a includes a power source terminal 900, a load circuit 901, a transmission buffer 902, a switch 903, a video terminal 904, and a switch 910. The load circuit 901 includes a switching control circuit 905 and an imager 906. At least one of the transmission buffer 902, the switch 903, and the switch 910 may be disposed in the imager 906. The processor 6 is the same as that shown in FIG. 2.

The transmission buffer 902 enters any one of a video output state (third state) and an output stoppage state (fourth state). When the state of the transmission buffer 902 is the video output state, the transmission buffer 902 outputs the video signal generated by the imager 906 to the video signal line 31. When the state of the transmission buffer 902 is the output stoppage state, the transmission buffer 902 stops the output of the video signal to the video signal line 31. The switch 910 (setting circuit) sets the state of the transmission buffer 902 to the video output state in the first period, and sets the state of the transmission buffer 902 to the output stoppage state in the second period.

The switch 910 is connected to the imager 906 and the transmission buffer 902. A gate terminal of the transmission buffer 902 is connected to the switch 910. The switch 910 connects the imager 906 and the transmission buffer 902 to each other in the first period and disconnects the imager 906 and the transmission buffer 902 from each other in the second period.

The switch 910 enters any one of the video output state and the output stoppage state. The switch 910 can switch between the video output state and the output stoppage state. When the state of the switch 910 is the video output state, the switch 910 connects the imager 906 and the transmission buffer 902 to each other. When the state of the switch 910 is the output stoppage state, the switch 910 disconnects the imager 906 and the transmission buffer 902 from each other.

The video signal is input to the switch 910 in the first period, and the switch 910 outputs the video signal to the transmission buffer 902. The transmission buffer 902 outputs the video signal to the video terminal 904.

A stoppage signal is input to the switch 910 in the second period, and the switch 910 outputs the stoppage signal to the transmission buffer 902. The stoppage signal has a fixed voltage. For example, the voltage of the stoppage signal is a ground voltage. The voltage of the stoppage signal may be the second power source voltage. The voltage of the stoppage signal may be a voltage between the ground voltage and the second power source voltage. Since the stoppage signal is input to the gate terminal of the transmission buffer 902, the voltage output from the transmission buffer 902 to the video terminal 904 does not change.

In the second embodiment, the endoscope system 1a can monitor a power source voltage provided to the imager 906 and does not prevent the miniaturization of the camera unit 9a as with the endoscope system 1 according to the first embodiment. In addition, since the transmission buffer 902 outputs a fixed voltage to the video terminal 904 in the second period, the endoscope system 1a can reduce the amount of noise mixed into the second power source voltage output from the video terminal 904 to the video signal line 31.

Third Embodiment

Figure 5:
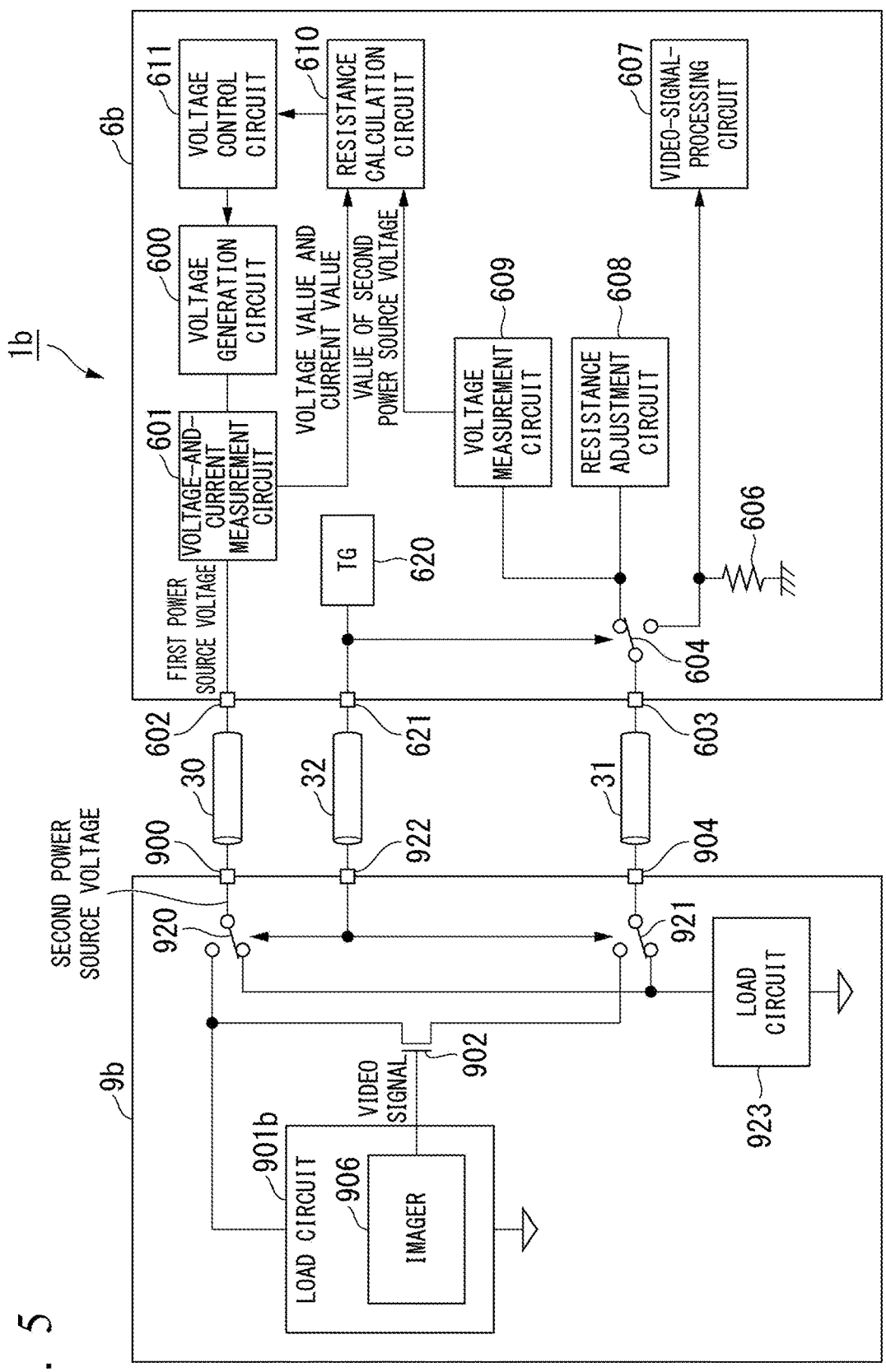
FIG. 5 is a block diagram showing a configuration of an endoscope system according to a third embodiment of the present invention.

FIG. 5 shows an internal configuration of an endoscope system 1b according to a third embodiment of the present invention. The same configuration as that shown in FIG. 2 will not be described. The endoscope system 1b shown in FIG. 5 includes a camera unit 9b and a processor 6b. The transmission cable 3 shown in FIG. 1 includes a power source line 30, a video signal line 31, and a control signal line 32 shown in FIG. 5. The camera unit 9b and the processor 6b are connected to each other by the power source line 30, the video signal line 31, and the control signal line 32.

The camera unit 9b includes a power source terminal 900, a load circuit 901b, a transmission buffer 902, a video terminal 904, a switch 920, a switch 921, a control terminal 922, and a load circuit 923. The load circuit 901b includes an imager 906. At least one of the transmission buffer 902, the switch 920, the switch 921, and the load circuit 923 may be disposed in the imager 906.

The processor 6b includes a voltage generation circuit 600, a voltage-and-current measurement circuit 601, a power source terminal 602, a video terminal 603, a switch 604, a resistor 606, a video-signal-processing circuit 607, a resistance adjustment circuit 608, a voltage measurement circuit 609, a resistance calculation circuit 610, a voltage control circuit 611, a timing generator (TG) 620, and a control terminal 621. All or part of the configuration of the processor 6b shown in HG. 5 may be disposed in the operation unit 4 or the connector unit 5 shown in FIG. 1.

The TG 620 generates a switching control signal used for controlling the state of each of the switches 604, 920, and 921. The TG 620 outputs the generated switching control signal to the switch 604 and the control terminal 621.

The state of the switch 604 is controlled based on the switching control signal generated by the TG 620. The state of the switch 604 is set to the video output state in the first period. At this time, the video signal transferred by the video signal line 31 and input to the video terminal 603 is output to the video-signal-processing circuit 607 via the switch 604. The state of the switch 604 is set to the power source output state in the second period. At this time, the second power source voltage transferred by the video signal line 31 and input to the video terminal 603 is output to the voltage measurement circuit 609 via the switch 604.

The switching control signal generated by the TG 620 is input to the control terminal 621. The control terminal 621 is connected to the control signal line 32. The control terminal 621 outputs the switching control signal to the control signal line 32. The control signal line 32 is a signal line disposed in the transmission cable 3. The control signal line 32 transfers the switching control signal output from the control terminal 621 to the camera unit 9b.

The control terminal 922 is connected to the control signal line 32. The switching control signal transferred by the control signal line 32 is input to the control terminal 922. The control terminal 922 outputs the switching control signal to the switch 920 and the switch 921.

The switch 920 and the switch 921 (first switching circuit) constitute a setting circuit. The switch 920 is connected to the power source terminal 900, the load circuit 901b, the switch 921, and the load circuit 923. The switch 921 is connected to the video terminal 904, the transmission buffer 902, and the switch 920.

The switch 920 and the switch 921 connect the power source line 30 and the video signal line 31 to each other in the second period and disconnect the power source line 30 and the video signal line 31 from each other in the first period. The switch 921 connects the transmission buffer 902 and the video signal line 31 to each other in the first period and disconnect the transmission buffer 902 and the video signal line 31 from each other in the second period. The switch 920 and the switch 921 connect the power source line 30 and the load circuit 923 to each other in the second period and disconnects the power source line 30 and the load circuit 923 from each other in the first period.

The switch 920 enters any one of an imager-driving state and a power source output state. The switch 920 can switch between the imager-driving state and the power source output state. When the state of the switch 920 is the imager-driving state, the switch 920 connects the power source line 30 and the load circuit 901b to each other, disconnects the power source line 30 and the switch 921 from each other, and disconnects the power source line 30 and the load circuit 923 from each other. When the state of the switch 920 is the power source output state, the switch 920 disconnects the power source line 30 and the load circuit 901b from each other, connects the power source line 30 and the switch 921 to each other, and connects the power source line 30 and the load circuit 923 to each other.

The state of the switch 920 is controlled based on the switching control signal output from the control terminal 922. The state of the switch 920 is set to the imager-driving state in the first period. At this time, the second power source voltage transferred by the power source line 30 and input to the power source terminal 900 is output to the imager 906 via the switch 920, and the imager 906 outputs the video signal. The state of the switch 920 is set to the power source output state in the second period. At this time, the second power source voltage transferred by the power source line 30 and input to the power source terminal 900 is output to the switch 921 and the load circuit 923 via the switch 920.

The load circuit 923 has a DC resistance value and consumes the second power source voltage as a current. For example, the load circuit 923 is a resistance element, a current source, or the like. Although a current flows through the load circuit 923, a current hardly flows though the video signal line 31.

The switch 921 enters any one of a video output state and a power source output state. The switch 921 can switch between the video output state and the power source output state. When the state of the switch 921 is the video output state, the switch 921 connects the transmission buffer 902 and the video signal line 31 to each other and disconnects the switch 920 and the video signal line 31 from each other. When the state of the switch 921 is the power source output state, the switch 921 disconnects the transmission buffer 902 and the video signal line 31 from each other and connects the switch 920 and the video signal line 31 to each other.

The state of the switch 921 is controlled based on the switching control signal output from the control terminal 922. The state of the switch 921 is set to the video output state in the first period. At this time, the transmission buffer 902 outputs the video signal to the video terminal 904. The state of the switch 921 is set to the power source output state in the second period. Since the state of each of the switches 920 and 921 is the power source output state in the second period, the power source line 30 and the video signal line 31 are short-circuited and the second power source voltage is output to the video terminal 904. Since the transmission buffer 902 and the video signal line 31 are disconnected from each other in the second period, the transmission buffer 902 stops the output of the video signal.

A switch control method in the third embodiment may be applied to the endoscope system 1 of the first embodiment or the endoscope system 1a of the second embodiment. In other words, in the endoscope system 1 or the endoscope system 1a, the control signal line 32 may be disposed, the switch 920 and the switch 921 may be disposed instead of the switch 903 and the switching control circuit 905, and the TG 620 may be disposed instead of the switching control circuit 605.

In the third embodiment, the endoscope system 1b can monitor a power source voltage provided to the imager 906 as with the endoscope system 1 according to the first embodiment.

Since the resistance value of the load circuit 923 is stable, a stable second power source voltage is output to the video signal line 31. Since the switching control circuit 605 (see FIG. 2) that generates the switching control signal is unnecessary, an increase of the circuit scale of the camera unit 9b is restricted.

Fourth Embodiment

Figure 6:
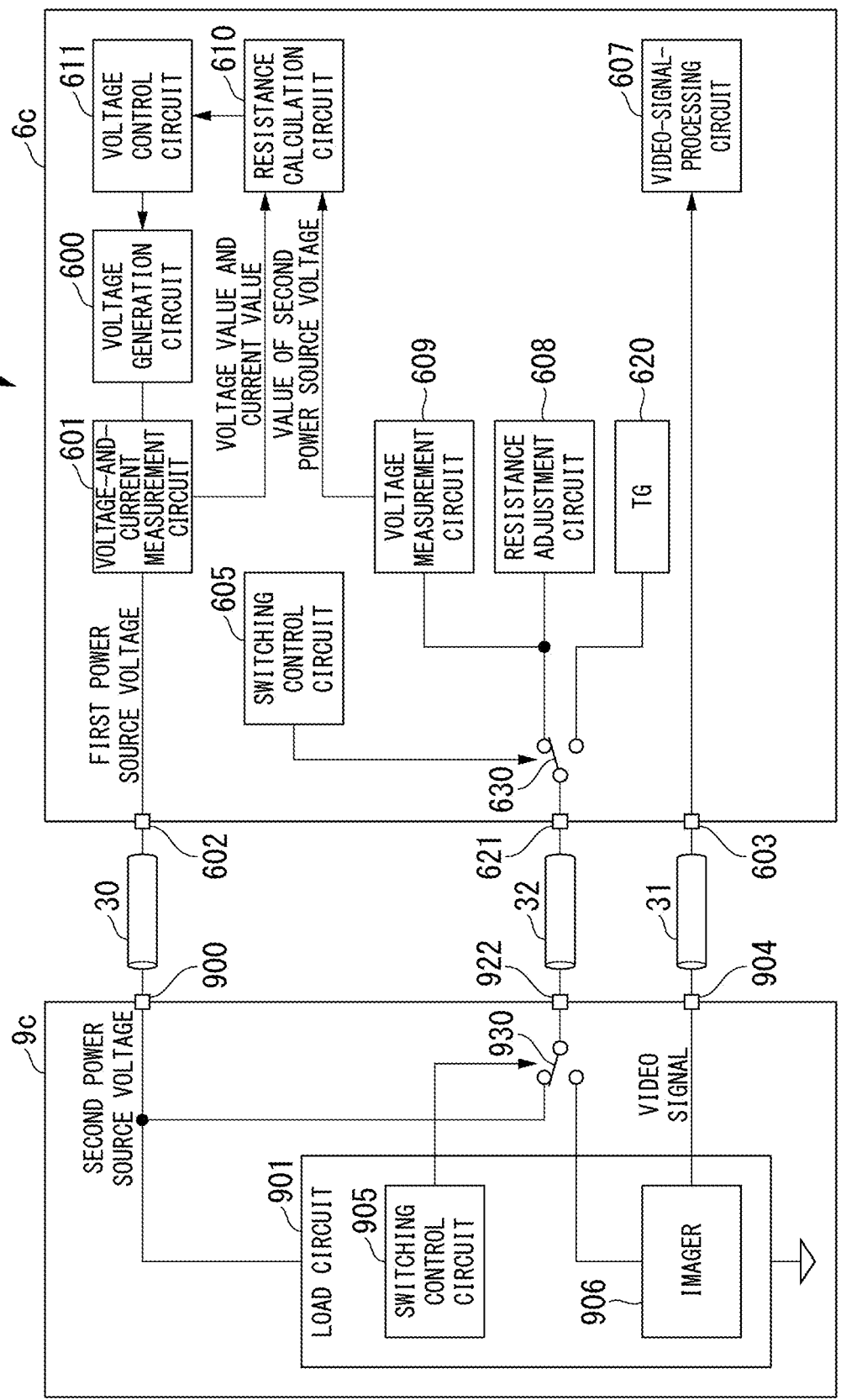
FIG. 6 is a block diagram showing a configuration of an endoscope system according to a fourth embodiment of the present invention.

FIG. 6 shows an internal configuration of an endoscope system 1c according to a fourth embodiment of the present invention. The same configuration as that shown in FIG. 2 will not be described. The endoscope system 1c shown in FIG. 6 includes a camera unit 9c and a processor 6c. The transmission cable 3 shown in FIG. 1 includes a power source line 30, a video signal line 31, and a control signal line 32 shown in FIG. 6. The camera unit 9c and the processor 6c are connected to each other by the power source line 30, the video signal line 31, and the control signal line 32.

The camera unit 9c includes a power source terminal 900, a load circuit 901, a video terminal 904, a control terminal 922, and a switch 930. The load circuit 901 includes a switching control circuit 905 and an imager 906. At least one of the switching control circuit 905 and the switch 930 may be disposed in the imager 906.

The processor 6c includes a voltage generation circuit 600, a voltage-and-current measurement circuit 601, a power source terminal 602, a video terminal 603, a switching control circuit 605, a video-signal-processing circuit 607, a resistance adjustment circuit 608, a voltage measurement circuit 609, a resistance calculation circuit 610, a voltage control circuit 611, a timing generator (TG) 620, a control terminal 621, and a switch 630. All or part of the configuration of the processor 6c shown in FIG. 6 may be disposed in the operation unit 4 or the connector unit 5 shown in FIG. 1.

The TG 620 (control signal generation circuit) generates an imager control signal used for controlling the state of the imager 906. For example, the imager control signal is a clock signal, a synchronization signal, a data signal, or the like. For example, the data signal is used for rewriting a value of a register that stores the state of the switching control circuit 905 of the imager 906. The TG 620 outputs the generated imager control signal to the switch 630.

The switch 630 (second switching circuit) constitutes a setting circuit. The switch 630 is connected to the control terminal 621, the voltage measurement circuit 609, and the TG 620. The switch 630 connects the control signal line 32 and the TG 620 to each other in the first period and disconnects the control signal line 32 and the TG 620 from each other in the second period. The switch 630 connects the control signal line 32 and the voltage measurement circuit 609 to each other in the second period and disconnects the control signal line 32 and the voltage measurement circuit 609 from each other in the first period.

The switch 630 enters any one of a control signal output state and a power source output state. The switch 630 can switch between the control signal output state and the power source output state. When the state of the switch 630 is the control signal output state, the switch 630 connects the control signal line 32 and the TG 620 to each other and disconnects the control signal line 32 and the voltage measurement circuit 609 from each other. When the state of the switch 630 is the power source output state, the switch 630 disconnects the control signal line 32 and the TG 620 from each other and connects the control signal line 32 and the voltage measurement circuit 609 to each other.

The switching control circuit 605 outputs a switching control signal to the switch 630, thus controlling the state of the switch 630. The switching control circuit 605 sets the state of the switch 630 to the control signal output state in the first period. At this time, the imager control signal output from the TG 620 is output to the control signal line 32 via the switch 630 and the control terminal 621. The switching control circuit 605 sets the state of the switch 630 to the power source output state in the second period. As described later, the control signal line 32 transfers the second power source voltage from the camera unit 9c to the processor 6c in the second period. The second power source voltage transferred by the control signal line 32 and input to the control terminal 621 is output to the voltage measurement circuit 609 via the switch 630.

The imager control signal generated by the TG 620 is input to the control terminal 621. The control terminal 621 is connected to the control signal line 32. The control terminal 621 outputs the imager control signal to the control signal line 32. The control signal line 32 transfers the imager control signal output from the control terminal 621 to the camera unit 9c.

The control terminal 922 is connected to the control signal line 32. The imager control signal transferred by the control signal line 32 is input to the control terminal 922. The control terminal 922 outputs the imager control signal to the switch 930.

The switch 930 (first switching circuit) constitutes a setting circuit. The switch 930 is connected to the control terminal 922, the power source terminal 900, and the imager 906. The switch 930 connects the power source line 30 and the control signal line 32 to each other in the second period and disconnects the power source line 30 and the control signal line 32 from each other in the first period. The switch 930 connects the imager 906 and the control signal line 32 to each other in the first period and disconnects the imager 906 and the control signal line 32 from each other in the second period.

The switch 930 enters any one of an imager control state and a power source output state. The switch 930 can switch between the imager control state and the power source output state. When the state of the switch 930 is the imager control state, the switch 930 connects the imager 906 and the control signal line 32 to each other and disconnects the power source line 30 and the control signal line 32 from each other. When the state of the switch 930 is the power source output state, the switch 930 disconnects the imager 906 and the control signal line 32 from each other and connects the power source line 30 and the control signal line 32 to each other.

The switching control circuit 905 outputs a switching control signal to the switch 930, thus controlling the state of the switch 930. The switching control circuit 905 sets the state of the switch 930 to the imager control state in the first period. At this time, the imager control signal transferred by the control signal line 32 and input to the control terminal 922 is output to the imager 906 via the switch 930. The imager 906 generates the video signal in accordance with the imager control signal by using the second power source voltage. The switching control circuit 905 sets the state of the switch 930 to the power source output state in the second period. At this time, the power source line 30 and the control signal line 32 are short-circuited, and the second power source voltage is output to the control terminal 922.

The control terminal 922 outputs the second power source voltage to the control signal line 32. The control signal line 32 transfers the second power source voltage output from the control terminal 922 to the processor 6c. The second power source voltage transferred by the control signal line 32 is input to the control terminal 621. The control terminal 621 outputs the second power source voltage to the voltage measurement circuit 609 via the switch 630.

The setting circuit including the switch 630 and the switch 930 sets the camera unit 9c and the processor 6c to be in a first state in the first period and sets the camera unit 9c and the processor 6c to be in a second state in the second period. The imager control signal is output to the control signal line 32 in the first state. The output of the imager control signal to the control signal line 32 is stopped in the second state. The load circuit 901 consumes the second power source voltage as a current in the second state. The second power source voltage is output to the control signal line 32 in the second state. The output of the second power source voltage to the control signal line 32 is stopped in the first state. The voltage measurement circuit 609 measures a value of the second power source voltage transferred by the control signal line 32.

The imager control signal is not provided to the imager 906 in the second period. The imager 906 can operate in accordance with the clock signal in the camera unit 9c in the second period.

In the fourth embodiment, the endoscope system 1c can monitor a power source voltage provided to the imager 906 as with the endoscope system 1 according to the first embodiment. The control signal line 32 is used for transferring the imager control signal and the second power source voltage, and the endoscope system 1c does not need to monitor the second power source voltage at all times. Therefore, a dedicated cable for transferring the second power source voltage is unnecessary, and the miniaturization of the camera unit 9c is not prevented.

The video signal line 31 is not used for transferring the second power source voltage. Therefore, the imager 906 can output the video signal also in the second period.

Fifth Embodiment

Figure 7:
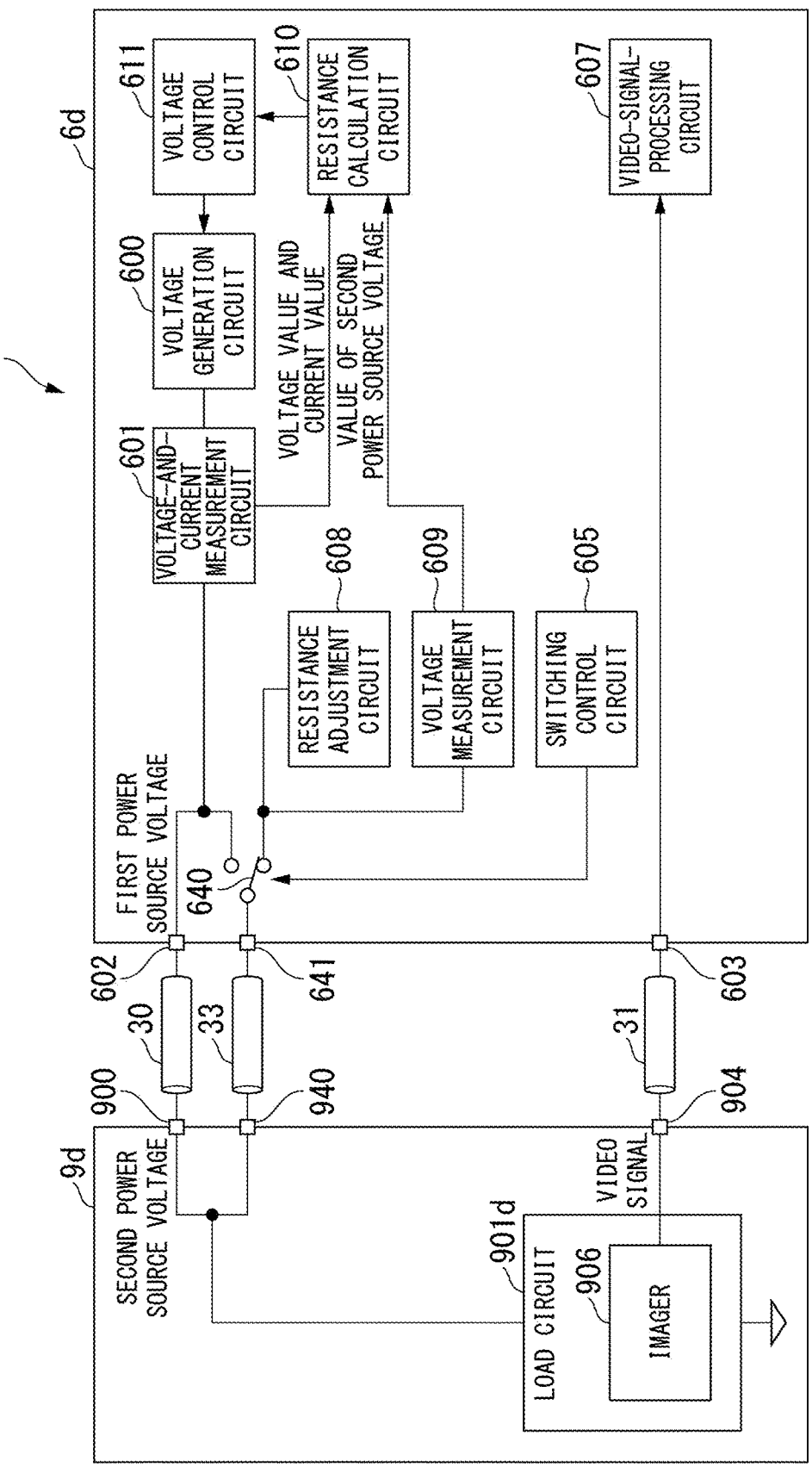
FIG. 7 is a block diagram showing a configuration of an endoscope system according to a fifth embodiment of the present invention.

FIG. 7 shows an internal configuration of an endoscope system 1d according to a fifth embodiment of the present invention. The same configuration as that shown in FIG. 2 will not be described. The endoscope system 1d shown in FIG. 7 includes a camera unit 9d and a processor 6d. The transmission cable 3 shown in FIG. 1 includes a power source line 30, a video signal line 31, and a power source line 33 shown in FIG. 7. The camera unit 9d and the processor 6d are connected to each other by the power source line 30, the video signal line 31, and the power source line 33.

The camera unit 9d includes a power source terminal 900, a load circuit 901d, a video terminal 904, and a power source terminal 940. The load circuit 901d includes an imager 906.

The processor 6d includes a voltage generation circuit 600, a voltage-and-current measurement circuit 601, a power source terminal 602, a video terminal 603, a switching control circuit 605, a video-signal-processing circuit 607, a resistance adjustment circuit 608, a voltage measurement circuit 609, a resistance calculation circuit 610, a voltage control circuit 611, a switch 640, and a power source terminal 641. All or part of the configuration of the processor 6d shown in FIG. 7 may be disposed in the operation unit 4 or the connector unit 5 shown in FIG. 1.

The switch 640 (second switching circuit) constitutes a setting circuit. The switch 640 is connected to the power source terminal 641, the voltage-and-current measurement circuit 601, and the voltage measurement circuit 609. The switch 640 connects the power source line 33 and the voltage-and-current measurement circuit 601 to each other in the first period and disconnects the power source line 33 and the voltage-and-current measurement circuit 601 from each other in the second period. The switch 640 connects the power source line 33 and the voltage measurement circuit 609 to each other in the second period and disconnects the power source line 33 and the voltage measurement circuit 609 from each other in the first period.

The switch 640 enters any one of a first power source output state and a second power source output state. The switch 640 can switch between the first power source output state and the second power source output state. When the state of the switch 640 is the first power source output state, the switch 640 connects the power source line 33 and the voltage-and-current measurement circuit 601 to each other and disconnects the power source line 33 and the voltage measurement circuit 609 from each other. When the state of the switch 640 is the second power source output state, the switch 640 disconnects the power source line 33 and the voltage-and-current measurement circuit 601 from each other and connects the power source line 33 and the voltage measurement circuit 609 to each other.

The switching control circuit 605 outputs a switching control signal to the switch 640, thus controlling the state of the switch 640. The switching control circuit 605 sets the state of the switch 640 to the first power source output state in the first period. At this time, the first power source voltage generated by the voltage generation circuit 600 is output to the power source line 30 via the power source terminal 602 and is output to the power source line 33 via the switch 640 and the power source terminal 641. The switching control circuit 605 sets the state of the switch 640 to the second power source output state in the second period. As described later, the power source line 33 transfers the second power source voltage from the camera unit 9d to the processor 6d in the second period. The second power source voltage transferred by the power source line 33 and input to the power source terminal 641 is output to the voltage measurement circuit 609 via the switch 640.

The state of the switch 640 is set to the first power source output state in the first period. The first power source voltage generated by the voltage generation circuit 600 is input to the power source terminal 641 via the voltage-and-current measurement circuit 601 and the switch 640 in the first period. The power source terminal 641 is connected to the power source line 33. The power source terminal 641 outputs the first power source voltage to the power source line 33. The power source line 33 is a signal line disposed in the transmission cable 3. For example, the sum of the cross-sectional area of the power source line 30 and the cross-sectional area of the power source line 33 is the same as the cross-sectional area of the power source line 30 shown in FIG. 2. The power source line 33 transfers the first power source voltage output from the power source terminal 641 to the camera unit 9d.

The power source terminal 940 is connected to the power source line 33. The first power source voltage transferred by the power source line 33 is input to the power source terminal 940. The power source terminal 940 outputs the first power source voltage to each circuit in the camera unit 9d as the second power source voltage. The first power source voltage is transferred to the camera unit 9d by both the power source line 30 and the power source line 33 in the first period.

The state of the switch 640 is set to the second power source output state in the second period. The power source line 33 and the voltage-and-current measurement circuit 601 are disconnected from each other, and the first power source voltage is transferred to the camera unit 9d only by the power source line 30.

The first power source voltage transferred by the power source line 30 is input to the power source terminal 900. The power source terminal 900 outputs the first power source voltage to the load circuit 901d and the power source terminal 940 as the second power source voltage. The power source terminal 940 outputs the second power source voltage to the power source line 33. The power source line 33 transfers the second power source voltage output from the power source terminal 940 to the processor 6d.

The second power source voltage transferred by the power source line 33 is input to the power source terminal 641. Since the power source line 33 and the voltage-and-current measurement circuit 601 are disconnected from each other and the power source line 33 and the voltage measurement circuit 609 are connected to each other, the power source terminal 641 outputs the second power source voltage to the voltage measurement circuit 609 via the switch 640.

The power source line 30 (first signal line) and the power source line 33 (second signal line) are connected in parallel to the camera unit 9d and the processor 6d. A setting circuit including the switch 640 sets the camera unit 9d and the processor 6d to be in the first state in the first period and sets the camera unit 9d and the processor 6d to be in the second state in the second period. The first power source voltage is transferred to the camera unit 9d by the power source line 30 and the power source line 33 in the first state. The load circuit 901d consumes the second power source voltage as a current in the second state. The second power source voltage is output to the power source line 33 in the second state. The voltage measurement circuit 609 measures a value of the second power source voltage transferred by the power source line 33.

In the fifth embodiment, the endoscope system 1d can monitor a power source voltage provided to the imager 906 as with the endoscope system 1 according to the first embodiment.

Since the switching control circuit 905 (see FIG. 2) that generates the switching control signal is unnecessary, an increase of the circuit scale of the camera unit 9d is restricted. The video signal line 31 is not used for transferring the second power source voltage. Therefore, the imager 906 can output the video signal also in the second period.

The first power source voltage is transferred to the camera unit 9d by the power source line 30 and the power source line 33 in the first period and is transferred to the camera unit 9d only by the power source line 30 in the second period. Since the resistance value of the power source line 30 is greater than a combined resistance value of the power source line 30 and the power source line 33, there is a possibility that the second power source voltage is likely to change due to the influence of the operation of the load circuit 901d. Therefore, there is a possibility that the characteristics of the video signal in the second period are different from those of the video signal in the first period. However, the endoscope system 1d can transfer the second power source voltage from the camera unit 9d to the processor 6d in the second period by allocating a blanking period to the second period or by allocating a period during which the imager 906 outputs a signal not required to be highly accurate to the second period.

Sixth Embodiment

Figure 8:
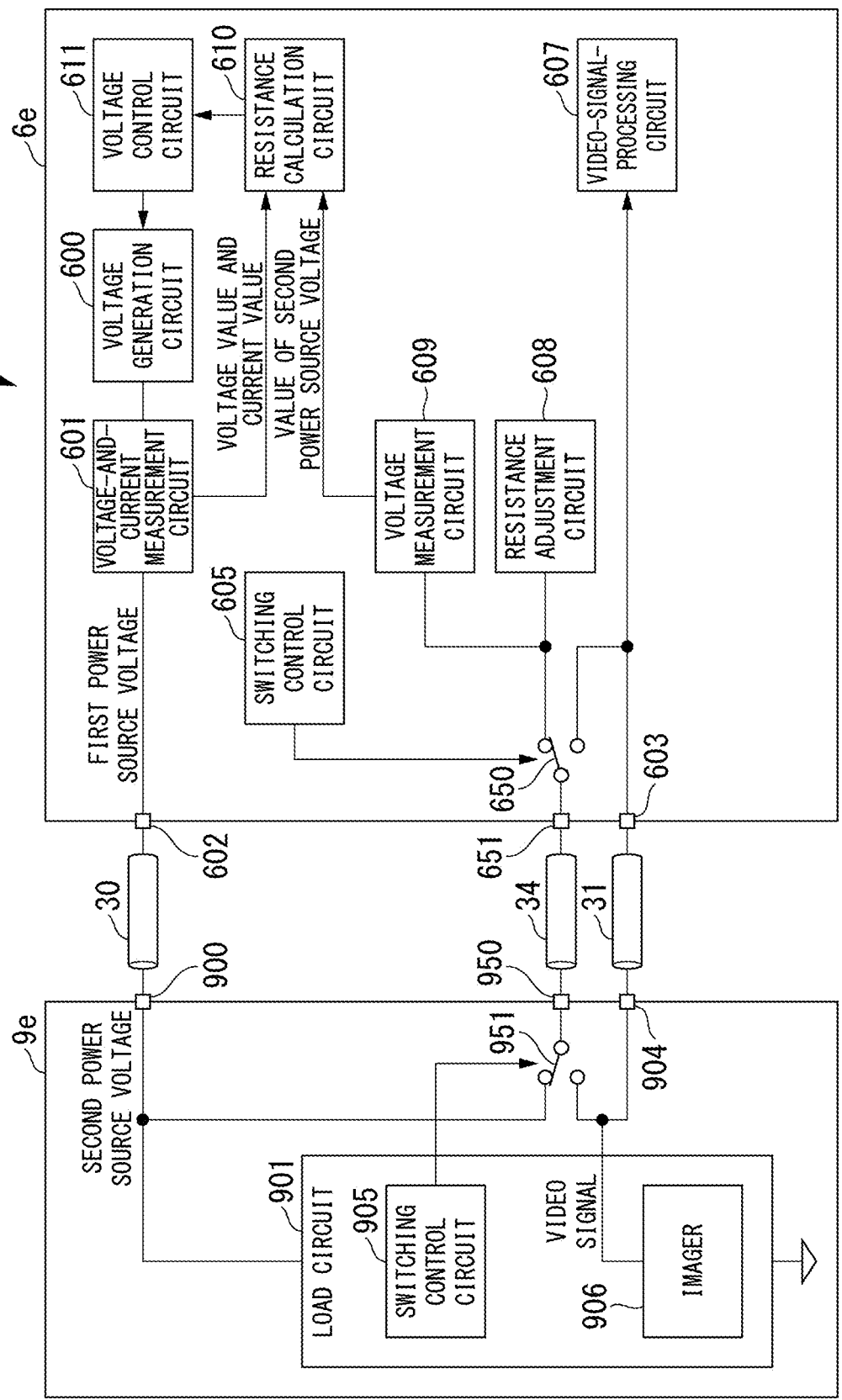
FIG. 8 is a block diagram showing a configuration of an endoscope system according to a sixth embodiment of the present invention.

FIG. 8 shows an internal configuration of an endoscope system 1e according to a sixth embodiment of the present invention. The same configuration as that shown in FIG. 2 will not be described. The endoscope system 1e shown in FIG. 8 includes a camera unit 9e and a processor 6e. The transmission cable 3 shown in FIG. 1 includes a power source line 30, a video signal line 31, and a video signal line 34 shown in FIG. 8. The camera unit 9e and the processor 6e are connected to each other by the power source line 30, the video signal line 31, and the video signal line 34.

The camera unit 9e includes a power source terminal 900, a load circuit 901, a video terminal 904, a video terminal 950, and a switch 951. The load circuit 901 includes a switching control circuit 905 and an imager 906. At least one of the switching control circuit 905 and the switch 951 may be disposed in the imager 906.

The processor 6e includes a voltage generation circuit 600, a voltage-and-current measurement circuit 601, a power source terminal 602, a video terminal 603, a switching control circuit 605, a video-signal-processing circuit 607, a resistance adjustment circuit 608, a voltage measurement circuit 609, a resistance calculation circuit 610, a voltage control circuit 611, a switch 650, and a video terminal 651. All or part of the configuration of the processor 6e shown in FIG. 8 may be disposed in the operation unit 4 or the connector unit 5 shown in FIG. 1.

The switch 951 (first switching circuit) constitutes a setting circuit. The switch 951 is connected to the video terminal 950, the power source terminal 900, and the imager 906. The switch 951 connects the power source line 30 and the video signal line 34 to each other in the second period and disconnects the power source line 30 and the video signal line 34 from each other in the first period. The switch 951 connects the imager 906 and the video signal line 34 to each other in the first period and disconnects the imager 906 and the video signal line 34 from each other in the second period.

The switch 951 enters any one of a video output state and a power source output state. The switch 951 can switch between the video output state and the power source output state. When the state of the switch 951 is the video output state, the switch 951 connects the imager 906 and the video signal line 34 to each other and disconnects the power source line 30 and the video signal line 34 from each other. When the state of the switch 951 is the power source output state, the switch 951 disconnects the imager 906 and the video signal line 34 from each other and connects the power source line 30 and the video signal line 34 to each other.

The switching control circuit 905 outputs a switching control signal to the switch 951, thus controlling the state of the switch 951. The switching control circuit 905 sets the state of the switch 951 to the video output state in the first period. At this time, the video signal output from the imager 906 is output to the video terminal 904 and is output to the video terminal 950 via the switch 951. The switching control circuit 905 sets the state of the switch 951 to the power source output state in the second period. At this time, the power source line 30 and the video signal line 34 are short-circuited, and the second power source voltage is output to the video terminal 950.

The video terminal 950 is connected to the video signal line 34. The video terminal 950 outputs the video signal or the second power source voltage to the video signal line 34. The video signal line 34 is a signal line disposed in the transmission cable 3. For example, the sum of the cross-sectional area of the video signal line 31 and the cross-sectional area of the video signal line 34 is the same as the cross-sectional area of the video signal line 31 shown in FIG. 2. The video signal line 34 transfers the video signal output from the imager 906 to the processor 6e in the first period. The video signal is transferred to the processor 6e by both the video signal line 31 and the video signal line 34 in the first period. For example, the video signal transferred to the processor 6e by both the video signal line 31 and the video signal line 34 may be a differential signal. The video signal line 34 transfers the second power source voltage output from the power source terminal 900 to the processor 6e in the second period.

The video terminal 651 is connected to the video signal line 34. The video signal or the second power source voltage transferred by the video signal line 34 is input to the video terminal 651.

The switch 650 (second switching circuit) constitutes a setting circuit. The switch 650 is connected to the video terminal 651, the voltage measurement circuit 609, and the video-signal-processing circuit 607. The switch 650 connects the video signal line 34 and the video-signal-processing circuit 607 to each other in the first period and disconnects the video signal line 34 and the video-signal-processing circuit 607 from each other in the second period. The switch 650 connects the video signal line 34 and the voltage measurement circuit 609 to each other in the second period and disconnects the video signal line 34 and the voltage measurement circuit 609 from each other in the first period.

The switch 650 enters any one of a video output state and a power source output state. The switch 650 can switch between the video output state and the power source output state. When the state of the switch 650 is the video output state, the switch 650 connects the video signal line 34 and the video-signal-processing circuit 607 to each other and disconnects the video signal line 34 and the voltage measurement circuit 609 from each other. When the state of the switch 650 is the power source output state, the switch 650 disconnects the video signal line 34 and the video-signal-processing circuit 607 from each other and connects the video signal line 34 and the voltage measurement circuit 609 to each other.

The switching control circuit 605 outputs a switching control signal to the switch 650, thus controlling the state of the switch 650. The switching control circuit 605 sets the state of the switch 650 to the video output state in the first period. At this time, the video signal transferred by the video signal line 34 and input to the video terminal 651 is output to the video-signal-processing circuit 607 via the switch 650. The switching control circuit 605 sets the state of the switch 650 to the power source output state in the second period. At this time, the second power source voltage transferred by the video signal line 34 and input to the video terminal 651 is output to the voltage measurement circuit 609 via the switch 650.

The video signal line 31 (first signal line) and the video signal line 34 (second signal line) are connected in parallel to the camera unit 9e and the processor 6e. A setting circuit including the switch 650 and the switch 951 sets the camera unit 9e and the processor 6e to be in the first state in the first period and sets the camera unit 9e and the processor 6e to be in the second state in the second period. The video signal is transferred to the processor 6e by the video signal line 31 and the video signal line 34 in the first state. The load circuit 901 consumes the second power source voltage as a current in the second state. The second power source voltage is output to the video signal line 34 in the second state. The voltage measurement circuit 609 measures a value of the second power source voltage transferred by the video signal line 34.

In the sixth embodiment, the endoscope system 1e can monitor a power source voltage provided to the imager 906 as with the endoscope system 1 according to the first embodiment.

The video signal line 31 is not used for transferring the second power source voltage. Therefore, the imager 906 can output the video signal also in the second period.

Since the resistance value of the video signal line 31 is greater than a combined resistance value of the video signal line 31 and the video signal line 34, there is a possibility that the characteristics of the video signal in the second period are different from those of the video signal in the first period. However, the endoscope system 1e can transfer the second power source voltage from the camera unit 9e to the processor 6e in the second period by allocating a blanking period to the second period or by allocating a period during which the imager 906 outputs a signal not required to be highly accurate to the second period.

Seventh Embodiment

Figure 9:
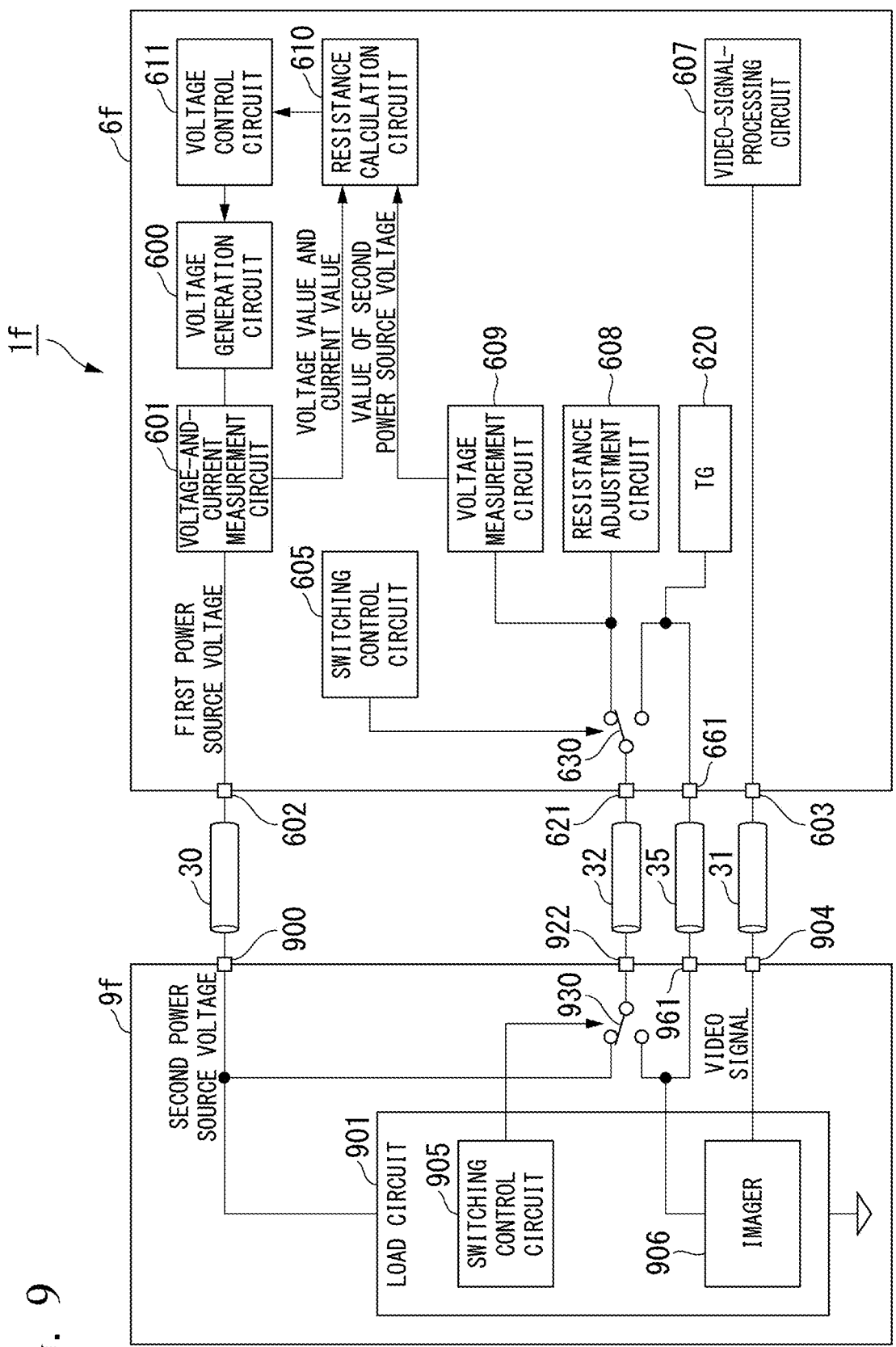
FIG. 9 is a block diagram showing a configuration of an endoscope system according to a seventh embodiment of the present invention.

FIG. 9 shows an internal configuration of an endoscope system 1f according to a seventh embodiment of the present invention. The same configuration as that shown in FIG. 2 will not be described. The endoscope system 1f shown in FIG. 9 includes a camera unit 9f and a processor 6f. The transmission cable 3 shown in FIG. 1 includes a power source line 30, a video signal line 31, a control signal line 32, and a control signal line 35 shown in FIG. 9. The camera unit 9f and the processor 6f are connected to each other by the power source line 30, the video signal line 31, the control signal line 32, and the control signal line 35.

The camera unit 9f includes a power source terminal 900, a load circuit 901, a video terminal 904, a control terminal 922, a switch 930, and a control terminal 961. The load circuit 901 includes a switching control circuit 905 and an imager 906. At least one of the switching control circuit 905 and the switch 930 may be disposed in the imager 906.

The processor 6f includes a voltage generation circuit 600, a voltage-and-current measurement circuit 601, a power source terminal 602, a video terminal 603, a switching control circuit 605, a video-signal-processing circuit 607, a resistance adjustment circuit 608, a voltage measurement circuit 609, a resistance calculation circuit 610, a voltage control circuit 611, a timing generator (TG) 620, a control terminal 621, a switch 630, and a control terminal 661. All or part of the configuration of the processor 6f shown in FIG. 9 may be disposed in the operation unit 4 or the connector unit 5 shown in FIG. 1.

The TG 620 (control signal generation circuit) generates an imager control signal used for controlling the state of the imager 906. The TG 620 outputs the generated imager control signal to the switch 630 and the control terminal 661.

The switch 630 (second switching circuit) constitutes a setting circuit. The switch 630 is connected to the control terminal 621, the voltage measurement circuit 609, and the TG 620. The switch 630 connects the control signal line 32 and the TG 620 to each other in the first period and disconnects the control signal line 32 and the TG 620 from each other in the second period. The switch 630 connects the control signal line 32 and the voltage measurement circuit 609 to each other in the second period and disconnects the control signal line 32 and the voltage measurement circuit 609 from each other in the first period.

The switch 630 enters any one of a control signal output state and a power source output state. The switch 630 can switch between the control signal output state and the power source output state. When the state of the switch 630 is the control signal output state, the switch 630 connects the control signal line 32 and the TG 620 to each other and disconnects the control signal line 32 and the voltage measurement circuit 609 from each other. When the state of the switch 630 is the power source output state, the switch 630 disconnects the control signal line 32 and the TG 620 from each other and connects the control signal line 32 and the voltage measurement circuit 609 to each other.

The switching control circuit 605 outputs a switching control signal to the switch 630, thus controlling the state of the switch 630. The switching control circuit 605 sets the state of the switch 630 to the control signal output state in the first period. At this time, the imager control signal output from the TG 620 is output to the control signal line 32 via the switch 630 and the control terminal 621 and is output to the control signal line 35 via the control terminal 661. The switching control circuit 605 sets the state of the switch 630 to the power source output state in the second period. As described later, the control signal line 32 transfers the second power source voltage from the camera unit 9f to the processor 6f in the second period. The second power source voltage transferred by the control signal line 32 and input to the control terminal 621 is output to the voltage measurement circuit 609 via the switch 630.

The imager control signal generated by the TG 620 is input to the control terminal 621 via the switch 630 and is input to the control terminal 661. The control terminal 621 is connected to the control signal line 32. The control terminal 621 outputs the imager control signal to the control signal line 32. The control signal line 32 transfers the imager control signal output from the control terminal 621 to the camera unit 9f.

The control terminal 661 is connected to the control signal line 35. The control terminal 661 outputs the imager control signal to the control signal line 35. The control signal line 35 is a signal line disposed in the transmission cable 3. For example, the sum of the cross-sectional area of the control signal line 32 and the cross-sectional area of the control signal line 35 is the same as the cross-sectional area of the control signal line 32 shown in FIG. 5. The control signal line 35 transfers the imager control signal output from the control terminal 661 to the camera unit 9f. The control signal is transferred to the camera unit 9f by both the control signal line 32 and the control signal line 35 in the first period. For example, the control signal transferred to the camera unit 9f by both the control signal line 32 and the control signal line 35 may be a differential signal.

The control terminal 922 is connected to the control signal line 32. The imager control signal transferred by the control signal line 32 is input to the control terminal 922. The control terminal 922 outputs the imager control signal to the switch 930.

The switch 930 (first switching circuit) constitutes a setting circuit. The switch 930 is connected to the control terminal 922, the power source terminal 900, and the imager 906. The switch 930 connects the power source line 30 and the control signal line 32 to each other in the second period and disconnects the power source line 30 and the control signal line 32 from each other in the first period. The switch 930 connects the imager 906 and the control signal line 32 to each other in the first period and disconnects the imager 906 and the control signal line 32 from each other in the second period.

The switch 930 enters any one of an imager control state and a power source output state. The switch 930 can switch between the imager control state and the power source output state. When the state of the switch 930 is the imager control state, the switch 930 connects the imager 906 and the control signal line 32 to each other and disconnects the power source line 30 and the control signal line 32 from each other. When the state of the switch 930 is the power source output state, the switch 930 disconnects the imager 906 and the control signal line 32 from each other and connects the power source line 30 and the control signal line 32 to each other.

The switching control circuit 905 outputs a switching control signal to the switch 930, thus controlling the state of the switch 930. The switching control circuit 905 sets the state of the switch 930 to the imager control state in the first period. At this time, the imager control signal transferred by the control signal line 32 and input to the control terminal 922 is output to the imager 906 via the switch 930. The imager 906 generates the video signal in accordance with the imager control signal by using the second power source voltage. The switching control circuit 905 sets the state of the switch 930 to the power source output state in the second period. At this time, the power source line 30 and the control signal line 32 are short-circuited, and the second power source voltage is output to the control terminal 922.

The control terminal 922 outputs the second power source voltage to the control signal line 32. The control signal line 32 transfers the second power source voltage output from the control terminal 922 to the processor 6f. The second power source voltage transferred by the control signal line 32 is input to the control terminal 621. The control terminal 621 outputs the second power source voltage to the voltage measurement circuit 609 via the switch 630.

The control terminal 961 is connected to the control signal line 35. The imager control signal transferred by the control signal line 35 is input to the control terminal 961. The control terminal 961 outputs the imager control signal to the imager 906.

The control signal line 32 (first signal line) and the control signal line 35 (second signal line) are connected in parallel to the camera unit 9f and the processor 6f. A setting circuit including the switch 630 and the switch 930 sets the camera unit 9f and the processor 6f to be in the first state in the first period and sets the camera unit 9f and the processor 6f to be in the second state in the second period. The imager control signal is transferred to the camera unit 9f by the control signal line 32 and the control signal line 35 in the first state. The load circuit 901 consumes the second power source voltage as a current in the second state. The second power source voltage is output to the control signal line 32 in the second state. The voltage measurement circuit 609 measures a value of the second power source voltage transferred by the control signal line 32.

In the seventh embodiment, the endoscope system 1f can monitor a power source voltage provided to the imager 906 as with the endoscope system 1 according to the first embodiment.

The video signal line 31 is not used for transferring the second power source voltage. Therefore, the imager 906 can output the video signal also in the second period.

The control signal line 35 is not used for transferring the second power source voltage. Therefore, the imager 906 can receive the control signal also in the second period.

Since the resistance value of the control signal line 35 is greater than a combined resistance value of the control signal line 32 and the control signal line 35, there is a possibility that the characteristics of the control signal in the second period are different from those of the control signal in the first period. However, the endoscope system 1f can transfer the second power source voltage from the camera unit 9f to the processor 6f by allocating a period during which the imager 906 receives a signal not required to be fast or highly accurate to the second period.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging device, comprising:
a camera unit including
an image sensor configured to receive a first power source voltage transferred by a power source line as a second power source voltage and generate a video signal,
wherein the video signal is output to a video signal line, and
a load circuit;
a control unit including
a signal reception circuit configured to receive the video signal,
a voltage generation circuit configured to output the first power source voltage to the power source line,
a voltage measurement circuit configured to measure a value of the second power source voltage, and
a voltage adjustment circuit configured to adjust a value of the first power source voltage by controlling the power source voltage generation circuit based on the value of the second power source voltage; and
a setting circuit configured to set the camera unit to be in a first state in a first period and set the camera unit to be in a second state in a second period different from the first period,
wherein the video signal generated by the image sensor is output to the video signal line in the first state,
wherein output of the video signal from the image sensor to the video signal line is stopped in the second state,
wherein the load circuit is configured to consume the second power source voltage as a current in the second state,
wherein the second power source voltage is output to the video signal line in the second state,
wherein output of the second power source voltage to the video signal line is stopped in the first state, and
wherein the voltage measurement circuit is configured to measure the value of the second power source voltage transferred by the video signal line.

2. The imaging device according to claim 1,
wherein the setting circuit includes:
a first switching circuit that is disposed in the camera unit and is configured to connect the power source line and the video signal line to each other in the second period and disconnect the power source line and the video signal line from each other in the first period; and
a second switching circuit that is disposed in the control unit and is configured to connect the video signal line and the signal reception circuit to each other in the first period, disconnect the video signal line and the signal reception circuit from each other in the second period, connect the video signal line and the voltage measurement circuit to each other in the second period, and disconnect the video signal line and the voltage measurement circuit from each other in the first period.

3. The imaging device according to claim 2, further comprising a resistance circuit including the voltage measurement circuit,
wherein the resistance circuit is configured to have a greater resistance value than a resistance value of the video signal line, and
wherein the second switching circuit is configured to connect the video signal line and the resistance circuit to each other in the second period and disconnect the video signal line and the resistance circuit from each other in the first period.

4. The imaging device according to claim 1,
wherein the camera unit further includes a transmission buffer configured to enter any one of a third state and a fourth state,
wherein, when a state of the transmission buffer is the third state, the transmission buffer is configured to output the video signal generated by the image sensor to the video signal line,
wherein, when the state of the transmission buffer is the fourth state, the transmission buffer is configured to stop output of the video signal to the video signal line, and
wherein the setting circuit is configured to set the state of the transmission buffer to the third state in the first period and set the state of the transmission buffer to the fourth state in the second period.

5. The imaging device according to claim 1,
wherein the voltage adjustment circuit is configured to calculate a resistance value of the power source line based on the value of the first power source voltage, the value of the second power source voltage, and a value of a current that flows through the power source line and adjust the value of the first power source voltage based on the resistance value.

6. An endoscope system, comprising:
a scope that has a distal end and is to be inserted into a living body; and
the imaging device according to claim 1,
wherein the camera unit is disposed in the distal end.

7. An imaging device, comprising:
a camera unit including
an image sensor configured to receive a first power source voltage transferred by a power source line as a second power source voltage, receive a control signal transferred by a control signal line, and generate a video signal in accordance with the control signal,
wherein the video signal is output to a video signal line, and
a load circuit;
a control unit including
a signal reception circuit configured to receive the video signal,
a control signal generation circuit configured to generate the control signal and output the generated control signal to the control signal line,
a voltage generation circuit configured to output the first power source voltage to the power source line,
a voltage measurement circuit configured to measure a value of the second power source voltage, and
a voltage adjustment circuit configured to adjust a value of the first power source voltage by controlling the power source voltage generation circuit based on the value of the second power source voltage; and a setting circuit configured to set the camera unit to be in a first state in a first period and set the camera unit to be in a second state in a second period different from the first period, wherein the control signal is output to the control signal line in the first state, wherein output of the control signal to the control signal line is stopped in the second state, wherein the load circuit is configured to consume the second power source voltage as a current in the second state, wherein the second power source voltage is output to the control signal line in the second state, wherein output of the second power source voltage to the control signal line is stopped in the first state, and wherein the voltage measurement circuit is configured to measure the value of the second power source voltage transferred by the control signal line.

8. An imaging device, comprising:

a camera unit including
an image sensor configured to receive a first power source voltage transferred by a power source line as a second power source voltage, receive a control signal transferred by a control signal line, and generate a video signal in accordance with the control signal,
wherein the video signal is output to a video signal line, and
a load circuit;

a control unit including
a signal reception circuit configured to receive the video signal,
a control signal generation circuit configured to generate the control signal and output the generated control signal to the control signal line,
a voltage generation circuit configured to output the first power source voltage to the power source line,
a voltage measurement circuit configured to measure a value of the second power source voltage, and
a voltage adjustment circuit configured to adjust a value of the first power source voltage by controlling the power source voltage generation circuit based on the value of the second power source voltage; and a setting circuit configured to set the camera unit to be in a first state in a first period and set the camera unit to be in a second state in a second period different from the first period, wherein any one of the power source line, the video signal line, and the control signal line includes a first signal line and a second signal line connected in parallel to the camera unit and the control unit, wherein any one of the first power source voltage, the video signal, and the control signal is transferred by the first signal line and the second signal line in the first state, wherein the load circuit is configured to consume the second power source voltage as a current in the second state, wherein the second power source voltage is output to any one of the first signal line and the second signal line in the second state, and wherein the voltage measurement circuit is configured to measure the value of the second power source voltage transferred by any one of the first signal line and the second signal line.

* * * * *